United States Patent [19]

Westgard et al.

[11] Patent Number: 5,633,166

[45] Date of Patent: May 27, 1997

[54] METHOD OF ANALYZING MEDICAL SPECIMENS WITH IMPROVED LENGTH OF ANALYTICAL RUN DETERMINATION

[75] Inventors: James O. Westgard, Madison, Wis.; Paul Mountain, Hamilton, Canada

[73] Assignee: MDS Health Group Limited, Etobicoke, Canada

[21] Appl. No.: 374,917

[22] Filed: Jan. 19, 1995

[51] Int. Cl.⁶ .................................................. G01N 31/00
[52] U.S. Cl. ............................. 436/8; 436/11; 436/12; 436/13; 436/14; 436/15; 436/16; 436/19
[58] Field of Search ................................. 436/8, 12–16, 436/19

[56] References Cited

U.S. PATENT DOCUMENTS 4,202,033  5/1980  Strobel .................................. 364/416

OTHER PUBLICATIONS

Clinical Chemistry, "Laboratory Process Specifications for Assuring Quality in the U.S. National Cholesterol Education Program", J. O. Westgard et al., vol. 37, No. 5, pp. 656–661 (1991).

Eur. J. Clin. Chem. Clin. Biochem., "Proposed Quality Specifications for the Imprecision and Inaccuracy of Analytical Systems for Clinical Chemistry", C.G. Fraser et al., vol. 30, No. 5, pp. 311–317 (1992).

Clinical Chemistry, "Tolerance Limits for Short–Term Analytical Bias and Analytical Imprecision Derived from Clinical Assay Specificity", G. G. Klee, vol. 39, No. 7, pp. 1514–1518 (1993).

D.W. Wilson, S.J. Gaskell, K.W. Kemp, "Quality Control in CLinical Endocrinology Proceedings of the Eighth Tenovus Workshop Cardiff May 1979", Alpha Omega Publishing Ltd., 1981, pp. 155–164.

James O. Westgard, Patricia L. Barry, Marian R. Hunt, Torgny Groth, "A Multi–Rule Shewhart Chart for Quality Control in Clinical Chemistry", CLinical Chemistry, 27, 492 (1981), pp. 493–501.

George S. Cembrowski, Elliot P. Chandler, James O. Westgard, "Assessment of Average of Normals Quality Control Procedures and Guidelines for Implementation", American Journal of Clinical Pathology, vol. 81, No. 4, Apr. 1984, pp. 492–499.

James O. Westgard, "OPSpecs® Manual Operating Specifications for Precision, Accuracy and Quality Control", WesTgard® QC, (WQC), Oct. 1994.

Amador et al. Am. J. Clin. Pathol. 1968, 50;369–378.
Begtrup et al. Scand. J. Clin, Lab. Invest. 1971;27;247–253.
Lewis et al. Clin. Chim Acta 1971;35;21–32.
Hoffman et al. Am. J. Clin. Pathol. 1965; 43:134–141.
Kilgariff et al Clin Chim Acta. 1968;19:175–179.

Primary Examiner—Paula K. Hutzell
Assistant Examiner—Rachel Heather Freed

[57] ABSTRACT

In high volume laboratory analysis of patient medical specimens, control materials are inserted at periodical intervals (e.g. once per eight hours) and analyzed. If the results of the analysis deviate from the mean according to statistical rules, the run of analyses prior to the insertion of control materials has in the past been rejected, often causing a substantial loss of results because the control materials were not inserted sufficiently frequently. According to the invention the patient mean of a test is determined, and when the mean deviates from the predetermined mean by more than a selected amount, this determination is used, not to reject the run, but rather to trigger insertion and analysis of control materials. If the analysis of control materials shows that the run is in control, the analyses made prior thereto are reported and the run is resumed. If the control material analysis shows that the run is out of control, then the prior analyses are rejected.

9 Claims, 6 Drawing Sheets

METHOD OF ANALYZING MEDICAL SPECIMENS WITH IMPROVED LENGTH OF ANALYTICAL RUN DETERMINATION

FIELD OF THE INVENTION

This invention relates to a method of analyzing patient medical specimens, and more particularly it relates to an improved method of controlling the quality of the analysis process.

BACKGROUND OF THE INVENTION

Patient medical specimens are commonly analyzed in high volume automated analyzers. Such analyzers, which are often capable of performing a number of tests, are produced by companies such as Kodak (the relevant division of which has been purchased by Johnson & Johnson), Miles Laboratories, Ciba Corning, Abbott Laboratories, Coulter, Medical Laboratory Analysis, and others. Many of these analyzers are quite complex; for example the Kodak E750-XRC analyzer is able to perform twenty-two tests on a single patient specimen, the tests being selectable by software input.

It is common practice in the use of such analyzers, and indeed mandated by government agencies in many countries (e.g. the HCFA in the U.S.) to check the quality of the results produced by the analyzers by periodically inserting control materials for analysis. The control materials, which are non-patient specimens prepared by commercial suppliers (frequently by the manufacturer of the analyzer in question) are analyzed by the instrument. If the results of the control material analysis vary from the required levels by more than a selected amount (the various tests used will be discussed), then the analyzer is considered to be functioning improperly.

Although the above-described method of quality control has been used in virtually all developed countries for many years, it has serious disadvantages. One disadvantage is that if as a result of analysis of a control material it is found that the analyzer is functioning improperly, then all of the patient specimens analyzed since the previous quality control check (at which time the analyzer was functioning properly) must, depending on the nature of the malfunction, be reconfirmed (and often re-analyzed). This is a costly and time consuming process.

A further disadvantage is that at the present time, there is no logical method for determining the length of an analytical run between insertion of control materials. In some cases there are government requirements, e.g. CLIA in the U.S. requires for many analyzers that control materials be inserted once every twenty-four hours. In practice laboratories may do so more frequently, e.g. once per shift (for example once every eight hours), to reduce the loss should it be found as a result of such an insertion that an analyzer is not functioning properly. However the same problem, namely the requirement to re-analyze patient specimens, still exists. In the extreme, to have complete confidence in the results it would be necessary to insert control materials after each analysis of a patient specimen, but this would obviously be impractical since it would be far too costly and time consuming.

An alternative procedure, referred to as the "Average of Normals" method of quality control, was described in an article by R. G. Hoffmann et al. entitled "The Average of Normals Method of Quality Control", American Journal of Clinical Pathology 1965; 43: 134–141, and has been described in more detail in an article by George Cembrowski, E. P. Chandler, and James O. Westgard entitled "Assessment of "Average of Normals" Quality Control Procedures and Guidelines for Implementation", American Journal of Clinical Pathology, Vol. 81, No. 4, April 1984. In the Average of Normals method, an error condition is signalled in an analytic process whenever the average of selected consecutive patient data is beyond the control limits established for the average of the patient population. When an error condition is signalled, the procedure is the same as that employed when a control material is inserted and an error is found in the analyzer response, namely the preceding run of analyses is rejected and the analyzer is inspected, recalibrated and if necessary repaired. The rejected analyses must then be re-performed before they can be reported to the laboratory's customers (usually physicians). The Average of Normals procedure has not been widely used since it requires detailed simulation studies for each analyte and method; it generally requires computer support to implement; it is not readily applicable when patient populations are unstable, and it is too difficult to make judgements from it as to whether a run should be rejected or reported.

BRIEF SUMMARY OF THE INVENTION

The invention provides a method of medical specimen analysis in which control materials are used to provide quality control checks at periodic intervals, but in which the length of the analytical run between quality control checks is determined according to a rational basis. According to the invention in one of its aspects there is provided a method of analyzing patient medical specimens comprising:

(a) analyzing on an analyzer a plurality of patient medical specimens to obtain a number representative of a selected characteristic of each such specimen, (b) determining a mean from at least some of said numbers, (c) determining whether said mean shifts by a preselected amount, (d) if said mean shifts by said preselected amount, then inserting a control material containing said selected characteristic and being of known properties into said analyzer, and analyzing said control material therein, (e) determining from the analysis of said control material whether or not said selected characteristic of said control material deviates from a selected standard by more than a predetermined amount.

Further advantages and aspects of the invention will appear from the following description, taken together with the accompanying drawings.

DETAILED DESCRIPTION OF PREFERRED EMBODIMENTS

Medical laboratories commonly analyze patient medical specimens (usually blood, urine or stools) for specific substances. The presence of these substances in the specimen, or the concentration of the substance in the specimen, is used by the medical profession as an aid in diagnosis, and sometimes as an alarm (to be reported immediately). A large variety of tests is available, usually performed in high volume on an automatic or semi-automatic basis by commercial analyzers which are available on the market. Typical such analyzers are listed after Table 1 below. These analyzers will analyze patient specimens to determine the levels of the substances shown for example in Table 1 below. Table 1 is purely exemplary of the many tests which may be performed on patient medical specimens.

TABLE 1

| TEST | REFERENCE OR THERAPEUTIC RANGE | IN-STRU-MENT | COMMERCIAL CONTROL MATERIAL (See Table 2 for Legend) |
|---|---|---|---|
| Acid Phosphatase | <1 IU/liter | K2 | 1 |
| Albumin (244 serum) | 35–50 grams/liter | K7 | 1 |
| Alkaline Phosphatase (serum) | 35–110 (adult) micrograms/liter | K7 | 1 |
| ALT (Alanine Transaminase) | 5–40 IU/liter | K7 | 1 |
| Amylase (serum) | Up to 95 micrograms/liter | K7 | 1 |
| AST (Aspartate Transaminase) | 5–40 IU/liter | K7 | 1 |
| Bilirubin Direct | Up to 8 micromoles/liter | K7 | 1 |
| Bilirubin Total | Up to 22 micromoles/liter | K7 | 1 |
| Bilirubin Pediatric Total | Up to 258 micromoles/liter (depending on age) | K7 | 1 |
| Urea | 1.5–8 millimoles/liter | K7 | 1 |
| Calcium | 2.12–2.62 millimoles/liter | K7 | 1 |
| Cholesterol | 5.20–6.20 millimoles/liter | K7 | 1 |
| Creatine Kinase | 45–240 (male), 25–180 (female) micromoles/liter | K7 | 1 |
| Creatine Kinase | 45–240 (male), 25–180 (female) micromoles/liter | IMx | 5 |
| Chloride | 95–110 millimoles/liter | K7 | 1 |
| Carbon Dioxide | 23–31 millimoles/liter | K7 | 1 |
| Creatinine | 60–125 (male), 50–110 (female) micromoles/liter | K7 | 1 |
| Iron | 14–29 (male), 11–27 (female) micromoles/liter | T | 7 |
| GGT (Gamma Glutamyl Transferase) | Up to 65 (male), up to 40 (female) micromoles/liter | K7 | 1 |
| Glucose | 3.6–6.4 micromoles/liter | K7 | 1 |
| HDL (High Density Lipid) Cholesterol | 0.77–1.68 (male), 0.90–2.07 (female) millimoles/liter | K7 | 1 |
| Lithium | 0.5–1.3 millimoles/liter | K7 | 1 |
| Lipase | Up to 200 micromoles/liter | K7 | 1 |
| Potassium | 3.5–5.2 millimoles/liter | K7 | 1 |
| LD (Lactate Dehydrogenase) | 100–240 micromoles/liter | K7 | 1 |
| Magnesium | 0.70–1.00 millimoles/liter | K7 | 1 |
| Sodium | 135–147 millimoles/liter | K7 | 1 |
| Phosphate | 0.80–1.45 millimoles/liter | K7 | 1 |
| TIBC (Total Iron Binding (Capacity) | 20–50% | T | 7 |
| Triglyceride | 0.35–2.75 (depending-on age and sex) millimoles/liter | K7 | 1 |
| Total Protein | 60–85 grams/liter | K7 | 1 |
| Urate | 230–480 micromoles/liter (adult male), 150–390 micromoles/ | K7 | 1 |

TABLE 1-continued

| TEST | REFERENCE OR THERAPEUTIC RANGE | IN-STRU-MENT | COMMERCIAL CONTROL MATERIAL (See Table 2 for Legend) |
|---|---|---|---|
| Digoxin | 0.2–2.6 nanomoles/liter | ACS | 3 |
| Ferritin | 30–255 micrograms/liter (adult male), 10–65 micrograms/liter (adult female) | ACS | 2 |
| Folate (275 blood) | >330 nanomoles/liter | Axsym | 2 |
| Free T4 (Free Thyrosine Index) | 13–53 | ACS | 2 |
| FSH (Follitropin hormone) | 2–8 IU/liter (adult male), 1–11 IU/liter (adult female follicular) | ACS | 2 |
| hCG (human chorionic Gonadotropin) | <5 (male), <5 (female, non-pregnant) | Axsym | 2 |
| IgE (Immunoglobulin E) | up to 450 micrograms/liter (adult) | ACS | 2 |
| LH (Lutropin hormone) | 2–6 IU/liter (adult male), 1–25 IU/liter (adult female, follicular) | ACS | 2 |
| Prolactin | up to 27 micrograins/liter | Axsym | 2 |
| Salicylate | 0.35–0.70 millimoles/liter (analgesic) | K2 | 6 |
| T Uptake (Triiodothyroxine Upt) | 0.35–0.45 | Axsym | 4 |
| Total T4 (Total Thyroxine) | 60–155 nanomoles/liter | Axsym | 4 |
| TSH (Thyrotropin Stimulating hormone) | 0.35–5.0 milli-IU/liter | ACS | 2 |
| Total T3 (Total Triiodothyroxine) | 1.2–3.1 nanomoles/liter | Axsym | 2 |
| Vitamin B12 | 120–150 picomoles/liter | Axsym | 2 |
| WBC (White Blood Cells) | $4.0$–$11 \times 10^9$/liter | STKS | 8 |
| RBC (Red Blood Cells) | $4.5$–$6.5 \times 10^{12}$/liter (adult male), $4.0$–$6.5 \times 10^{12}$/liter (adult female) | STKS | 8 |
| Platelets | $150$–$400 \times 10^9$/liter | STKS | 8 |
| MCV (Mean Cell Volume) | 80–100 microns$^3$ | STKS | 8 |
| HCT (Hematocrit) | 0.4–0.54 (adult male), 0.35–0.47 (adult female) | STKS | 8 |
| Hb (Hemoglobin) | 135–180 grams/liter (adult male), 115–165 grams/liter (adult female) | STKS | 8 |
| PT/INR (Prothrombin Time/INR) | $13.0 \pm 1.0$ (seconds) | MLA | 9 |
| APTT (Activated Partial Thromboplastin Time) | $29 \pm 6$ (seconds) | MLA | 9 |

In Table 1 above, the symbols K2, etc. are short forms for the following instruments:

K2—Kodak (Johnson & Johnson) E250, by Johnson & Johnson

K7—Kodak (Johnson & Johnson) E750XRC, by Johnson & Johnson

T—Miles Technicon RA-1000, by Miles Laboratories

ACS—Ciba Corning ACS:180, by Ciba Corning

Axsym—Abbott Axsym, by Abbott Laboratories

IMx—Abbott IMx, by Abbott Laboratories

STKS—Coulter STKS, by Coulter

MLA—MLA 1000, by Medical Laboratory Automation

As mentioned, the quality of the output of the analyzers is checked at selected intervals by inserting known control materials for analysis. The control materials are supplied both by the instrument manufacturers and by other companies. Table 2 below lists typical control material suppliers with reference to the legend in Table 1.

TABLE 2

| CONTROL MATERIAL SUPPLIER | LEGEND |
|---|---|
| Kodak Ektachem Performance Verifier Controls - 2 levels | 1 |
| Biorad Lyphochek Immunoassay Controls - 3 levels | 2 |
| Biorad Therapeutic Drug Monitoring Controls - 3 levels | 3 |
| Abbott T3 Uptake Controls - 3 levels | 4 |
| Abbott Ck-2 Controls - 3 levels | 5 |
| Kodak Liquid Performance Verifier Controls - 2 levels | 6 |
| Coulter Serachem Controls - 2 levels | 7 |
| Coulter SC - 3 levels | 8 |
| Dade Citrol - 3 levels | 9 |

Usually each control material is provided in at least two concentration levels, one inside the normal range in which the patient's results are expected to fall, and one outside the range. For example if a value below the expected range is not a medical problem but a value elevated above the expected range is a concern, then the first concentration level of control material will be within the expected range and the second will be in the elevated range. In some cases three concentration levels of control materials are provided, one below, one within and one above the expected range.

As mentioned, it has for some time been required, e.g. in the U.S., that medical specimen analysis, which is usually conducted in high volume at specialized laboratories using analyzers such as those mentioned, be monitored with statistical quality control. The control focuses on analyzing control materials, plotting the results on control charts, and taking action when the analysis of a control material produces a result which is beyond a predetermined limit. The action taken, besides rechecking using another sample of quality control material, has been invariably to reject the run (by not reporting the analyses obtained), thus requiring repeat analyses of the specimens in question. Therefore considerable effort has been devoted to creating control rules which will maximize the probability of detecting errors in the analysis while minimizing the probability of false rejections.

In the U.S., minimum standards have been set by the Clinical Laboratory Improvement Amendments of 1988 (CLIA-88). CLIA-88 requires that when control materials are used, statistical parameters such as the mean and standard deviation for each lot number of control material be determined through repetitive testing. CLIA also sets analytical quality or proficiency testing criteria for acceptable performance. Table 3 below sets out the CLIA proficiency testing criteria for acceptable analytical quality. These are the minimum standards which must be met by an analytical laboratory, but higher standards may be needed depending on the clinical requirements of the physician users and patient customers of the laboratory.

TABLE 3

CLIA proficiency testing criteria for acceptable analytical quality [Federal Register Feb. 28, 1992; 57(40):7002–186]

| Routine Chemistry Test or Analyte | Acceptable Performance |
|---|---|
| Alanine aminotransferase (ALT) | Target value ±20% |
| Albumin | Target value ±10% |
| Alkaline phosphatase | Target value ±30% |
| Amylase | Target value ±30% |
| Aspartate Aminotransferase (AST) | Target value ±20% |
| Bilirubin, total | Target value ±0.4 mg/dL or ±20% (greater) |
| Blood gas pO$_2$ | Target value ±3 SD |
| Blood gas pCO$_2$ | Target value ±5 mm Hg or ±8% (greater) |
| Blood gas pH | Target value ±0.04 |
| Calcium, total | Target value ±1.0 mg/dL |
| Chloride | Target value ±5% |
| Cholesterol, total | Target value ±10% |
| Cholesterol, high density lipoprotein | Target value ±30% |
| Creatine kinase | Target value ±30% |
| Creatine kinase isoenzymes | MB elevated (present or absent) or Target value ±3 SD |
| Creatinine | Target value ±0.3 mg/dL or ±15% (greater) |
| Glucose | Target value ±6 mg/dL or ±10% (greater) |

TABLE 3-continued

CLIA proficiency testing criteria for acceptable analytical quality [Federal Register Feb. 28, 1992; 57(40):7002–186]

| | |
|---|---|
| Iron, total | Target value ±20% |
| Lactate dehydrogenase (LDH) | Target value ±20% |
| LDH isoenzymes | LDH1/LDH2 (+ or −) or Target value ±30% |
| Magnesium | Target value ±25% |
| Potassium | Target value ±0.5 mmol/L |
| Sodium | Target value ±4 mmol/L |
| Total protein | Target value ±10% |
| Triglycerides | Target value ±25% |
| Urea Nitrogen | Target value ±2 mg/dL or ±9% (greater) |
| Uric acid | Target value ±17% |

| Endocrinology Test or Analysis | Acceptable Performance |
|---|---|
| Cortisol | Target value ±25% |
| Free thyroxine | Target value ±3 SD |
| Human chorionic gonadotropin | Target value ±3 SD or (positive or negative) |
| T$_3$ uptake | Target value ±3 SD method |
| Triiodothyronine | Target value ±3 SD |
| Thyroid stimulating hormone | Target value ±3 SD |
| Thyroxine | Target value ±20% or 1.0 mcg/dL (greater) |

| General Immunology Test or Analyte | Acceptable Performance |
|---|---|
| Alpha-1 antitrypsin | Target value ±3 SD |
| Alpha-fetoprotein | Target value ±3 SD |
| Antinuclear antibody | Target value ±2 dilution or (pos. or neg.) |
| Antistreptolysin O | Target value ±2 dilution or (pos. or neg.) |
| Anti-Human Immunodeficiency virus | Reaction or nonreactive |
| Complement C3 | Target value ±3 SD |
| Complement C4 | Target value ±3 SD |
| Hepatitis (HBSAG, anti-HBc, HBeAg) | Reactive (positive) or nonreactive (negative) |
| IgA | Target value ±3 SD |
| IgE | Target value ±3 SD |
| IgG | Target value ±25% |
| IgM | Target value ±3 SD |
| Infectious mononucleosis | Target value ±2 dilution or (pos. or neg.) |
| Rheumatoid factor | Target value ±2 dilution or (pos. or neg.) |
| Rubella | Target value ±2 dilution or (pos. or neg.) |

| Toxicology Test or Analyte | Acceptable Performance |
|---|---|
| Alcohol, blood | Target value ±25% |
| Blood lead | Target value ±10% or ±4 mcg/dL (greater) |
| Carbamazepine | Target value ±25% |
| Digoxin | Target value ±20% or 0.2 ng/mL (greater) |
| Ethosuximide | Target value ±20% |
| Gentamicin | Target value ±25% |
| Lithium | Target value ±0.3 mmol/L or ±20% (greater) |
| Phenobarbital | Target value ±20% |
| Phenytoin | Target value ±25% |
| Primidone | Target value ±25% |
| Procainamide (and metabolite) | Target value ±25% |
| Quinidine | Target value ±25% |
| Theophylline | Target value ±25% |

TABLE 3-continued

CLIA proficiency testing criteria for acceptable analytical quality [Federal Register Feb. 28, 1992; 57(40):7002-186]

| Tobramycin | Target value ±25% |
|---|---|
| Valproic acid | Target value ±25% |

| Hematology Test or Analyte | Acceptable Performance |
|---|---|
| Cell identification | 90% or greater consensus on identification |
| White cell differentiation | Target ±3 SD based on percentage of different types of white cells |
| Erythrocyte count | Target ±6% |
| Hematocrit | Target ±6% |
| Hemoglobin | Target ±7% |
| Leukocyte count | Target ±15% |
| Platelet count | Target ±25% |
| Fibrinogen | Target ±20% |
| Partial thromboplastin time | Target ±15% |
| Prothrombin time | Target ±15% |

As will be seen, the requirements for analytical quality can be presented as absolute concentration limits, or as a percentage (i.e. target value plus or minus a percentage) or as a distribution of a survey group (e.g. target value plus or minus a given number of standard deviations).

The control rules which have been used are based on the mean of the desired characteristic of the control material and on its standard deviation. As is well known, the mean x is determined by the equation $$\bar{x} = \Sigma x_i / n$$

where $x_i$ is an individual measurement and n is the number of measurements. The standard deviation s describes the dispersion of a set of measurements about the mean and is calculated from the equation $$s = \sqrt{[n\Sigma x_i^2 - (\Sigma x_i)^2]/[n(n-1)]}$$

The control rules in common use include the following:

| 1. | $1_{2s}$ | This means that a run is rejected as being out of control when one control measurement in the group or control measurements of control materials (N) exceeds control limits set as the mean ± 2s, where the mean and s (standard deviation) are determined from the particular control material being tested. |
|---|---|---|
| 2. | $1_{2.5s}$ | This means that the run is rejected when one control measurement exceeds control limits set as the mean ± 2.5s. |
| 3. | $1_{3s}$ | This means that the run is rejected when one control measurement exceeds control limits set as the mean ± 3s. |
| 4. | $1_{3.5s}$ | This means that the run is rejected when one control measurement exceeds control limits set as the mean ± 3.5s. |

Multi-rule quality control procedures can also be formed, by selecting a combination of control rules that are sensitive to either random or systematic error. The $1_{3s}$ rule is often used as the initial rule. However the detection of systematic errors may be improved by use of the following control rules:

| $2_{2s}$ | The run is rejected when two consecutive control measurements exceed the same limit, either the mean plus 2s or the mean minus 2s. |
|---|---|
| $4_{1s}$ | The run is rejected when four consecutive control measurements exceed the same mean plus 1s or mean minus 1s control limit. |
| $10_x$ | The run is rejected when ten consecutive control measurements fall on one side of the mean. |
| $R_{4s}$ | The run is rejected when one control measurement exceeds the mean plus 2s and another exceeds the mean minus 2s. |

Multi-rule quality control procedures in common use include the $1_{3s}/2_{2s}/R_{4s}$ rules with N=2, and $1_{3s}/2_{2s}/R_{4s}/4_{1s}$ with N=4. These quality control procedures attempt to maximize error detection by the parallel application of multiple rules and to minimize false rejections by the choice of individual rules all having a low probability for false rejection.

An important problem for many years has been: once control materials have been analyzed and no errors detected, and a run has been started, when should control materials be tested again? Minimum standards have been set by CLIA. CLIA requires that control materials be analyzed after each analytical run, which it defines as follows: "A run is an interval within which the accuracy and precision of a testing system is expected to be stable, but cannot be greater than 24 hours . . . ". CLIA also requires that for quantitative tests, the laboratory must provide at least two samples of different concentrations of control materials "not less frequently than once each run of specimens". This establishes a minimum number of control measurements of two per run, one on each of two different control materials. Most laboratories analyze control materials more frequently than this, because they do not wish to "lose" too many results if an error is detected. The frequency of analyzing control materials is usually based on experience and is largely arbitrary. However because it is costly to insert and analyze control materials, the maximum number of control measurements used in most laboratories is four measurements per run (two replicates at two different levels), e.g. at 8 hour intervals. Thus Ns from two to four are commonly used in most health care laboratories.

The operation of conventional control methods will next be described. If when an analyzer is working properly its results were always consistently identical when analyzing control materials, then it would only be necessary, during control material analysis, to look for a deviation greater than the allowable deviation (e.g. as set by CLIA). However in real life analyzers there is normal inaccuracy and imprecision in the measurement method, and these must be taken into account.

Therefore the usual way of describing quality control performance is by (a) the probability for rejecting runs when the performance is in fact stable and the runs should not have been rejected, and by (b) the probability of rejecting a run when the performance is in fact unstable. The probability of false rejection is referred to as $P_{fr}$ and the probability of detecting unstable performance, i.e. an error, is referred to as $P_{ed}$, which describes how often a run will be rejected when systematic or random errors are present in addition to the stable imprecision of the measurement procedure.

Ideally low false rejection and high error detection are desired, for example a $P_{fr}$ of 0.01 together with a $P_{ed}$ of 0.90.

In practice less ideal values may be acceptable in some situations. For example $P_{ed}$ values of 0.50 may be practical for analytical systems that have high stability and a low frequency of problems.

Figure 1:
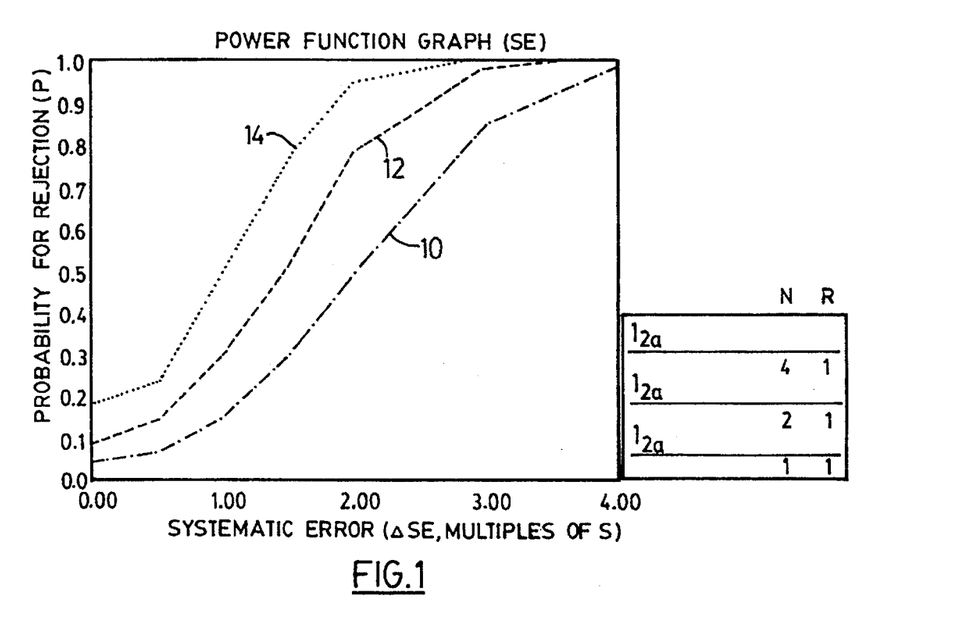
FIG. 1 is a power function graph showing probability of error detection plotted against systematic error.

The probabilities for rejecting different sizes of error are normally presented using power function graphs, where "power" refers to the statistical power or the capability for rejecting a run. In a power function graph the probability that a run will be rejected is plotted on the y-axis versus the size of the error occurring on the x-axis. Two graphs are usually presented, one for systematic error (SE) and one for random error (RE). FIG. 1 illustrates a power graph showing the probability of rejecting runs having systematic errors when using a $1_{2s}$ control rule (a Levy-Jennings chart with control limits set at mean±2s). Curve 10, 12 and 14 are for Ns of 1, 2 and 4 respectively. The applicable N, and the number of runs R, are shown at the side of the graph.

Figure 2:
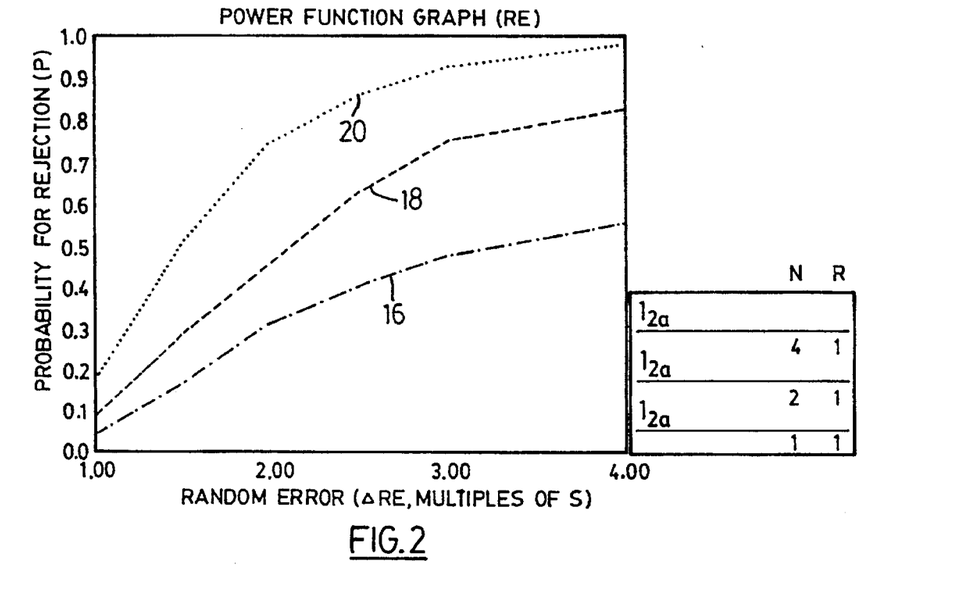
FIG. 2 is a power function graph showing probability of error detection plotted against random error.

FIG. 2 is a power function graph similar to that of FIG. 1 and illustrating the probability of rejecting runs having random errors using the same $1_{2s}$ control rule with Ns of 1, 2 and 4 (curves 16, 18 and 20 respectively).

The power function graphs are used to determine whether the quality control procedures achieve the required quality in routine testing.

It will be seen that the x-axis in FIG. 1 begins with a value of 0.0, which is the smallest value for systematic error, meaning that the measurement procedure operates only with its own stable bias and not with any additional bias due to unstable performance. In FIG. 2 the x-axis begins at 1.0, which is the smallest random error, meaning that the measurement procedure is operating with its stable standard deviation or its inherent imprecision.

It will be seen that the probability for rejection increases as N increases, demonstrating, as common sense would predict, that more control measurements provide better detection of analytical disturbances.

The probability for false rejection is estimated from the y-intercept of the power curve for the N of interest. For the $1_{2s}$ rule with N=1, for example $P_{fr}$ is seen to be 0.05, which means that one out of twenty control measurements are expected to fall outside of control limits set as the mean±2s. $P_{fr}$ increases as N increases, becoming 0.09 for N=2 and 0.18 for N=4. False rejection rates of 5% to 18% are expected for a $1_{2s}$ control rule with commonly used Ns. These high false rejection rates will cause much time and effort to be wasted investigating and repeating analytical runs which do not have problems. Because of this, the use of $1_{2s}$ control rules, although widely adopted in the past, has not been recommended by some experts in the field. More commonly, multi-rule procedures are used instead.

It is common to calculate the critical analytical errors which need to be detected by the quality control procedures to ensure that the test results meet the desired (e.g. the CLIA) standards. For example for total cholesterol, the total allowable error in proficiency testing ($TE_{PT}$) is 10%, and it is important to know the systematic and random errors that need to be detected to ensure that the test results are good to within 10% of their correct values.

The critical systematic error $\Delta SE_{crit}$ and the critical random error $\Delta RE_{crit}$ can be calculated from the following equations:

$$\Delta SE_{crit} = [(TE_{PT} - \text{bias}_{meas})/s_{meas}] - 1.65 \quad (1)$$

$$\Delta RE_{crit} = (TE_{PT} - \text{bias}_{meas})/1.65 s_{meas} \quad (2)$$

In equations 1 and 2 above, $\text{bias}_{meas}$ is the inaccuracy of the measurement procedure and $s_{meas}$ is the imprecision of the measurement procedure. The imprecision $s_{meas}$ of the measurement procedure is determined by taking a single sample and testing it repeatedly, and then determining the mean and the standard deviation. The standard deviation is referred to as $s_{meas}$.

To determine the inaccuracy $\text{bias}_{meas}$, a group of different patient samples are run on an analyzer using a new reagent (e.g. 50 to 100 specimens), and the results are plotted on the y-axis. The specimens are also analyzed using a comparison method known to be correct whose results are plotted on the x-axis, and a correlation line is determined, from which the systematic differences or bias are estimated (as is well known in the field).

The number 1.65 is a "z-value" which describes the portion of the error distribution that is permitted to exceed the quality requirements before the process is to be stopped. A z-value of 1.65 corresponds to allowing a 5% defect rate before rejecting a run as being out of control.

To illustrate the above equations, consider a cholesterol method where as mentioned $TE_{PT}$ is 10%, and where $s_{meas}$ is 2.0%, and $\text{bias}_{meas}$ is 2.0%. Then:

$$\Delta SE_{crit} = [(10-2)/2] - 1.65 = 2.35$$

$$\Delta RE_{crit} = (10-2)/1.65*2 = 2.42$$

This means that in the above example, a systematic error that is 2.35 times the standard deviation of a method, or a random error that causes a 2.42-fold increase in the standard deviation, needs to be detected by the quality control procedure to ensure that test results are good to within 10% of their correct value. Errors having these values or larger must be detected by the quality control procedure.

Figure 3:
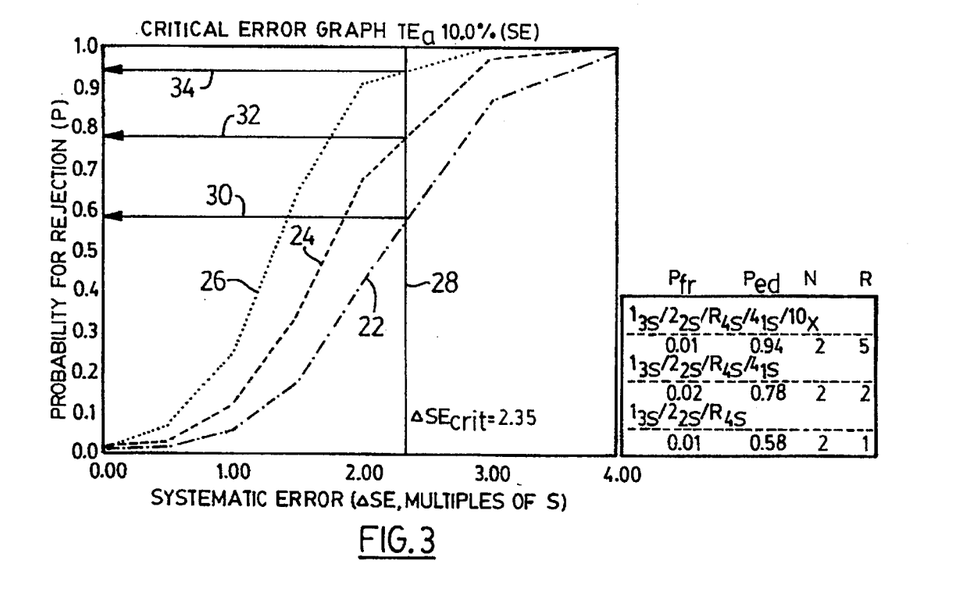
FIG. 3 is graph similar to that of FIG. 1 but showing a method of determining the probability of detecting a critical systematic error.

Once critical size errors are known, power function graphs may be used to determine the probability of detecting such critical size errors, as well as the probability for false rejections. As shown in FIG. 3, which shows curves 22, 24, 26 for the quality control rules indicated at the right hand side of the figure, the desired power curve (depending on N and the number of runs R) is selected and then a vertical line 28 is drawn up from the value $\Delta SE_{crit} = 2.35$ on the x-axis. Where the vertical line intercepts the power curve having the N of interest, a horizontal line 30, 32 or 34 is drawn to intersect the y-axis, and the probability of error detection is read at that point.

Figure 4:
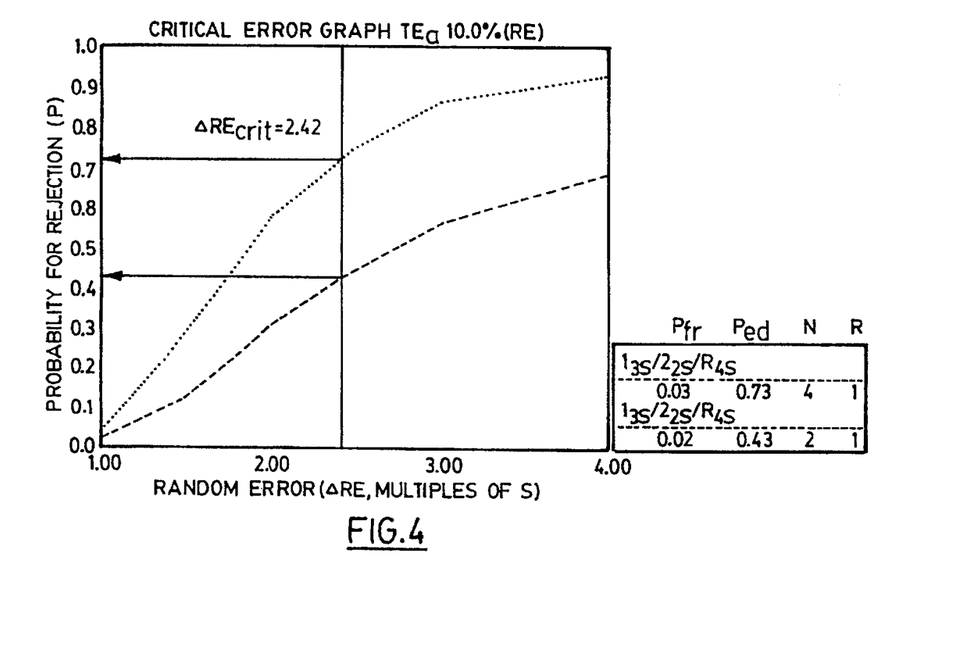
FIG. 4 is a graph similar to that of FIG. 2 but showing a method of determining the probability of detecting a critical random error.
Figure 5A:
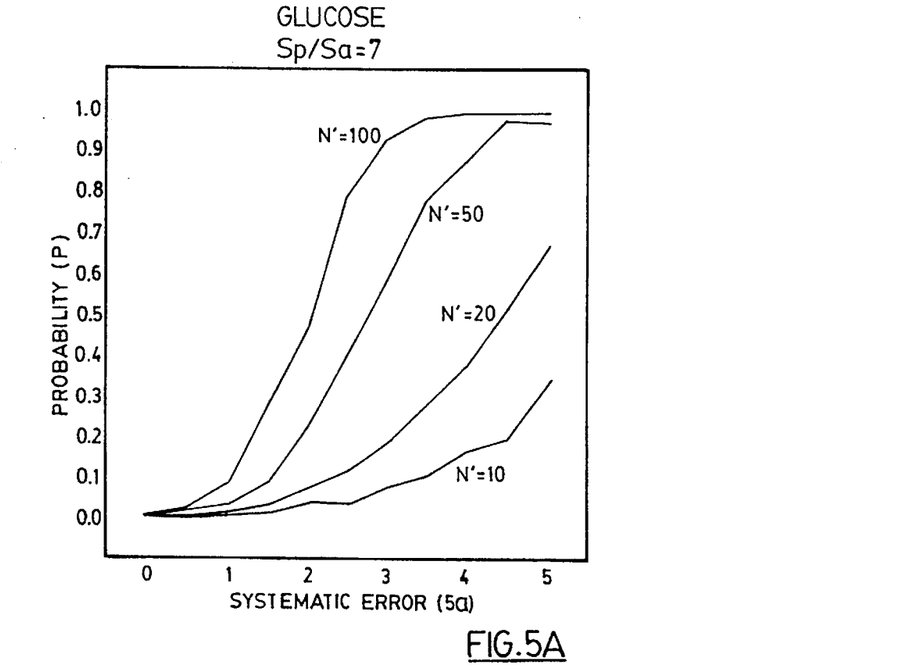
FIGS. 5A, 5B, 5C and 5D are power function graphs showing the probability of detecting errors for various substances and ratios of population standard deviation to analytic standard deviation.
Figure 5B:
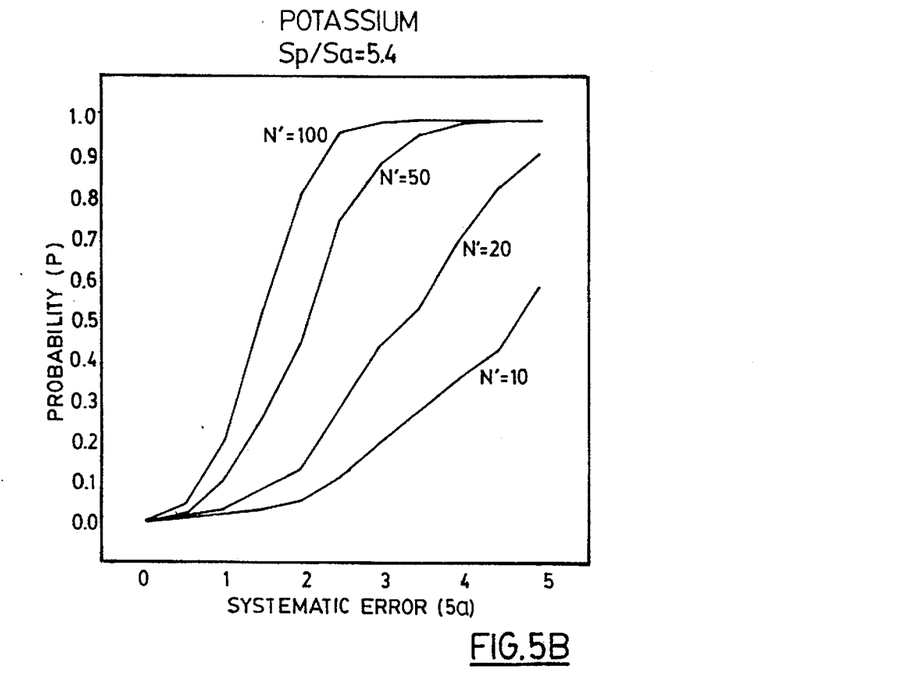
Figure 5C:
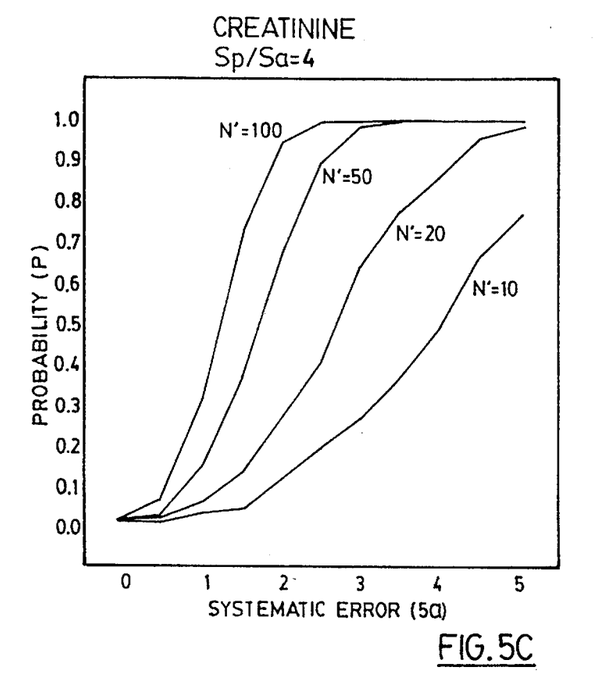
Figure 5D:
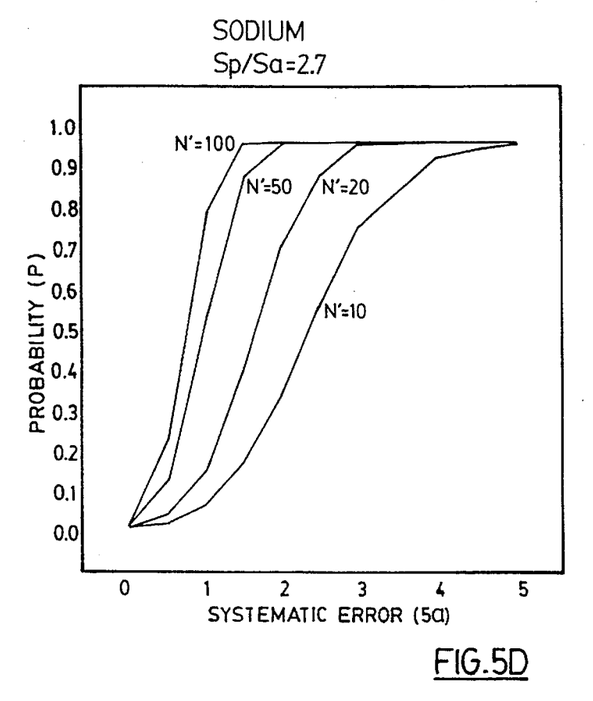

For example for cholesterol, FIG. 3 shows that the probabilities for error detection ($P_{ed}$) are 0.58, 0.78 and 0.94 depending on the number of runs and the rules chosen. FIG. 4 shows corresponding probabilities for detecting the critical random error $\Delta RE_{crit}$. In both cases the probability of false rejection (the Y-intercept) is quite low.

By way of example, the assessment of probabilities for false rejection and error detection for a cholesterol measurement procedure where $TE_{PT}$ is 10%, $s_{meas}$ is 2.0%, and $\text{bias}_{tot}$ is 2.0%, is shown in Table 4 below. In Table 4, the use of three different choices of quality control (QC) rules is illustrated.

TABLE 4

Assessment of the probabilities for false rejection and error detection for a cholesterol measurement procedure where $TE_{PT}$ is 10%, $s_{meas}$ is 2.0%, and $\text{bias}_{tot}$ is 2.0%

| QC Rules | N(run) | $P_{fr}$ | $P_{ed}$ ($\Delta SE_{crit} = 2.35$) | $P_{ed}$ ($\Delta RE_{crit} = 2.42$) |
|---|---|---|---|---|
| $1_{2s}$ | 1 | 0.05 | 0.61 | 0.39 |
|  | 2 | 0.09 | 0.85 | 0.60 |

TABLE 4-continued

Assessment of the probabilities for false rejection and error detection for a cholesterol measurement procedure where $TE_{PT}$ is 10%, $s_{meas}$ is 2.0%, and $bias_{tot}$ is 2.0%

| QC Rules | N(run) | $P_{fr}$ | $P_{ed}$ ($\Delta SE_{crit}$ = 2.35) | $P_{ed}$ ($\Delta RE_{crit}$ = 2.42) |
|---|---|---|---|---|
| | 4 | 0.18 | 0.96 | 0.84 |
| $1_{3s}$ | 2 | 0.01 | 0.47 | 0.34 |
| | 4 | 0.01 | 0.64 | 0.58 |
| $1_{3s}/2_{2s}/$ | 2 (run 1) | 0.02 | 0.58 | 0.43 |
| $R_{4s}/4_{1s}/$ | (run 2) | 0.02 | 0.78 | |
| $10_x$ | (run 5) | 0.02 | 0.94 | |
| | 4 (run 1) | 0.03 | 0.87 | 0.73 |
| | (run 3) | 0.03 | 0.98 | |

It will be seen that with this cholesterol example, the best choices for quality control rules or procedures for high error detection probability would be a $1_{2s}$ rule with N=2–4 or $1_{3s}/2_{2s}/R_{4s}/4_{1s}/10_x$ with N=4 control limit. However use of 2s control limits with Ns of 2 to 4 would lead to a 9% to 18% false rejection rate, which would not be cost effective. By comparison the multi-rule procedure with N=4 has a false rejection rate of only 3% and would provide nearly 90% error detection.

In some cases either $s_{meas}$ (the imprecision of the measurement) or the $bias_{tot}$ (the total inaccuracy of the measurement) is so high that application of the ordinary quality control rules will lead either to too low a probability of detecting critical errors, or to too high a false rejection rate. Using conventional quality control methods, these tests need improvements in their precision and/or accuracy, or otherwise they will be difficult to control with quality control procedures having a reasonable number of control measurements. Table 5 below lists typical tests, the target or typical values expected to be present, the total allowable error $TE_{PT}$, $s_{meas}$, $bias_{tot}$ and $\Delta SE_{crit}$.

TABLE 5

Calculation of $\Delta SE_{crit}$

| Test Name | Units | Target Value | $TE_{PT}$ | $s_{meas}$ | $Bias_{tot}$ | $\Delta SE_{crit}$ |
|---|---|---|---|---|---|---|
| Potassium | mmol/L | 5.0 | 10% | 1.0% | 3.0% | 5.35s |
| Glucose | mg/dL | 120 | 10 | 1.5 | 3.0 | 3.02 |
| Calcium | mg/dL | 10.0 | 10 | 2.0 | 3.0 | 1.85 |
| Albumin | g/dL | 3.5 | 10 | 2.0 | 2.0 | 2.35 |
| Total Protein | g/dL | 8.0 | 10 | 2.0 | 1.0 | 2.85 |
| Urea Nitrogen | mg/dL | 20.0 | 10 | 2.0 | 0.0 | 3.35 |
| Bilirubin | mg/dL | 4.0 | 10 | 2.5 | 0.0 | 2.35 |
| Cholesterol | mg/dL | 200 | 10 | 3.0 | 0.0 | 1.68 |

Where $\Delta SE_{crit}$ is high, e.g. for potassium, it is possible with simple control rules to have a high probability of detecting errors of the critical error magnitude and a low probability of false rejections. Where $\Delta SE_{crit}$ is relatively low, e.g. for calcium or cholesterol, it is much more difficult to achieve a high probability of error detection with a low false rejection probability.

This is illustrated in Table 6 below, which is calculated from known power function graphs and which shows the probabilities of error detection $P_{ed}$ and false rejection $P_{fr}$. In Table 6 the levels or concentrations of control materials analyzed are indicated as L (low), M (medium) or H (high).

TABLE 6

Probabilities for Run Rejection from Power Function Graphs

| Test | Levels Of Control L,M,H | Total Number Controls (N) | Control Rules | Assessment of QC Performance | | |
|---|---|---|---|---|---|---|
| | | | | $\Delta SE_{crit}$ | $P_{fr}$ | $P_{ed}$ |
| Potassium | L,H | 2 | $1_{3s}$ | 5.35s | 0.01 | 0.99 |
| Glucose | L,M | 2 | $1_{3s}$ | 3.02 | 0.01 | 0.94 |
| Calcium | M,H | 4 | $1_{3s}$ | 1.85 | 0.01 | 0.41 |
| Albumin | L,H | 4 | $1_{3s}$ | 2.35 | 0.01 | 0.65 |
| Total Protein | L,H | 4 | $1_{3s}$ | 2.85 | 0.01 | 0.85 |
| Urea Nitrogen | M,H | 2 | $1_{3s}$ | 3.35 | 0.01 | 0.83 |
| Bilirubin | L,M | 4 | $1_{3s}$ | 2.35 | 0.01 | 0.65 |
| Cholesterol | M,H | 4 | $1_{3s}$ | 1.68 | 0.01 | 0.34 |

It will be seen that using the $1_{3s}$ control rule with N of 2–4, the probability of false rejection is in all cases very low (0.01), meaning that fewer than 1% of runs having stable performance would be expected to be rejected. However the probability of error detection ranges from 0.99 for potassium to 0.34 for cholesterol. For potassium nearly all runs having the critical size systematic error would be detected. For cholesterol only 34% of runs having the critical systematic error would be rejected. In practice this means that for cholesterol, the control rules must be changed and/or N must be increased, thus increasing the cost and time needed for quality control testing.

Graphical tools have been used in the past which show the relationship between the imprecision and inaccuracy of a measurement procedure, and the quality control needed to achieve a defined quality requirement with a known level of assurance. These operating specification charts can be derived as set forth in Section 3 (see particularly pages 3–4 and 3–5) of the publication entitled "OPSpecs® Manual" published October, 1994 by Westgard Quality Corporation. The contents of such publication are incorporated by reference herein.

Although the above known quality control procedures yield good results in most cases, they cannot readily control with the required degree of assurance the analysis of some substances, without increasing N (the number of quality control measurements) to an uneconomic degree. In addition if an analyzer malfunctions (e.g. a temperature controller fails), this will not be detected until the end of a run, by which time numerous analyses will have to be rejected.

Therefore, according to the invention an additional element is added to the quality control procedure. Specifically, the mean of the test results for the specimen analyses is determined, and then the extent to which such mean shifts is monitored. If the mean shifts by greater than a selected amount, typically by $\Delta SE_{crit}$, indicating a medically important shift in the mean, no judgement is made at this point as to whether or not to report the data or conversely to reject the analytical run. Instead, such shift is used as a criteria to re-evaluate the analytical run by inserting a control material and performing a control measurement. In other words, the shift is used to end the analytical run (by inserting control materials) but not to reject the run. So far as is known, this approach is unique. In the past, analytical run length has been arbitrary (e.g. the CLIA requirements) or based on a combination of experience and cost considerations, but has never been determined on a logical basis.

It will be appreciated that this method of determining analytical run length is most useful when a relatively normal population is being screened, e.g. when the specimens being tested contain in at least substantial part specimens from patients who are simply undergoing medical check-ups, or who may have minor ailments. The method is more prone to signalling unnecessary run endings with smaller hospital populations where the test results tend to have wider variations.

In the method of the invention, a minimum number of specimens N' to establish a mean for a given test must first be established. (N' is used to distinguish from the N previously described, which was the number of control material measurements.) The number N' will depend on the individual variations in the measured analyte. Where the variation is small, N' may be as low as about 40, or even lower. Where the inter-individual variation is higher, N' may need to be between 300 and 600. A discussion of the factors involved in determining the mean is contained in the above-identified paper entitled "Assessment of "Average of Normals" Quality Control Procedures and Guidelines for Implementation" by G. S. Cembrowski, E. P. Chandler and James O. Westgard (which paper is hereby incorporated by reference). As there described, the performance of the procedure is affected by the ratio of the variation in the population to analytic variation, N' (the number of patient results averaged), the control limits chosen, the truncation limits chosen, and the percentage of the population lying adjacent to the truncation limits. However since according to the invention a shift in the patient mean is used not to reject an analytical run, but rather to end a run by inserting known control materials, therefore a higher probability of "false rejection" is acceptable than would otherwise be the case. This is because the consequence of "false rejection" is simply that an unnecessary quality control check has been made, and not that a large number of prior analyses have been rejected and must be re-run.

Table 7 below (from the Cembrowski et al. paper, Table 1) shows, for a number of analytes, typical population means $x_p$, typical population standard deviations $s_p$, typical analytic standard deviations $s_a$, and the rations $s_p/s_a$.

TABLE 7

Population Mean ($x_p$), Population Standard Deviation ($s_p$), Analytic Standard Deviation, $s_a$ and $s_p/s_a$

| Analyte | $x_p$ | $s_p$ | $s_a$ | $s_p/s_a$ |
|---|---|---|---|---|
| Sodium (mmol/L) | 142.0 | 3.57 | 1.34 | 2.7 |
| Potassium (mmol/L) | 4.3 | 0.43 | 0.080 | 5.4 |
| Chloride (mmol/L) | 103.6 | 3.46 | 1.21 | 2.9 |
| $CO_2$ (mmol/L) | 25.2 | 6.59 | 0.84 | 7.8 |
| Glucose (mg/dL) | 93.6 | 11.5 | 1.65 | 7.0 |
| Urea Nitrogen (mg/dL) | 14.4 | 5.46 | 0.42 | 13.0 |
| Creatinine (mg/dL) | 0.89 | 0.28 | 0.070 | 4.0 |
| Calcium (mg/dL) | 9.6 | 0.47 | 0.18 | 2.6 |
| Phosphorus (mg/dL) | 3.6 | 0.66 | 0.096 | 6.9 |
| Uric acid (mg/dL) | 5.1 | 1.43 | 0.17 | 8.4 |
| Cholesterol (mg/dL) | 170.0 | 34.4 | 3.8 | 9.1 |
| Total protein (g/dL) | 6.9 | 0.62 | 0.13 | 4.8 |
| Albumin (g/dL) | 3.9 | 0.44 | 0.12 | 3.7 |
| Total bilirubin (mg/dL) | 0.4 | 0.19 | 0.066 | 2.9 |
| Gamma glutamyl transpeptidase (U/L) | 31.0 | 20.0 | 3.15 | 6.3 |
| Alkaline Phosphatase (U/L) | 78.0 | 23.7 | 2.3 | 10.0 |
| Aspartate aminotransferase (U/L) | 33.0 | 13.8 | 6.95 | 2.0 |
| Lactate dehydrogenase (U/L) | 157.0 | 40.1 | 7.38 | 5.4 |

As described and shown in the Cembrowski et al. paper, FIGS. 5A to 5D show the effects of varying the number of patient results (N') that are averaged by the average of normals procedure. Systematic error $\Delta SE$ is plotted on the x-axis and probability of error detection on the y-axis. The number N' for each curve is shown adjacent each curve. In the FIGS. 5A to 5D power curves the control limits have been calculated to provide a probability of false rejection of about 1%. It will be seen that the probability of error detection is higher with greater N', and is also higher for a given N' and given $\Delta SE$ when the ratio $s_p/s_a$ is smaller (as would be expected).

Figure 6:
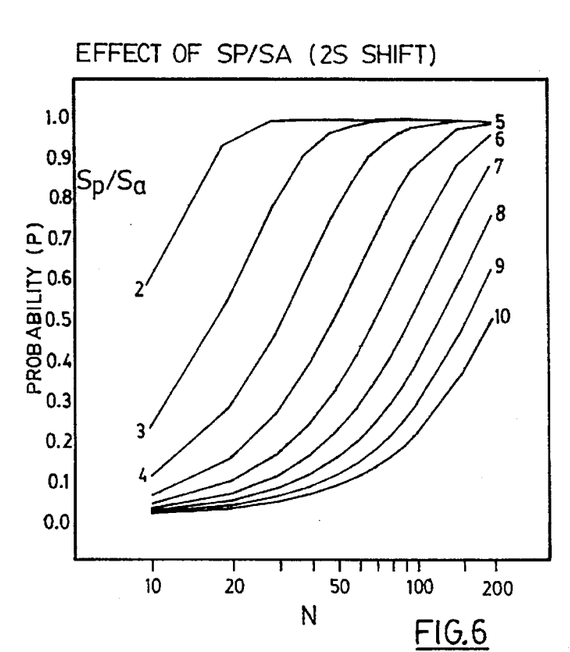
FIG. 6 is a nomogram plotting probability of error detection versus number of patient samples.

As also described and shown in the Cembrowski et al. paper, FIG. 6 is a nomogram showing the effect of differing ratios $s_p/s_a$ on the detection of a systematic error $\Delta SE=2s_a$. The probability of detection is plotted on the y-axis and N' (in logarithmic scale) is plotted on the x-axis. The values of $s_p/s_a$ for each curve are shown adjacent each curve. Curves such as those of FIG. 6, which show how error detection varies with N' and with the ratio $s_p/s_a$, will help to choose the appropriate N' for each analyte of interest.

Preferably in the method of the invention, N' is selected by superimposing the calculated $\Delta SE_{crit}$ value on the power curves having the appropriate $s_p/s_a$ ratio for the characteristic of interest. An example of this is illustrated in FIG. 7.

Figure 7:
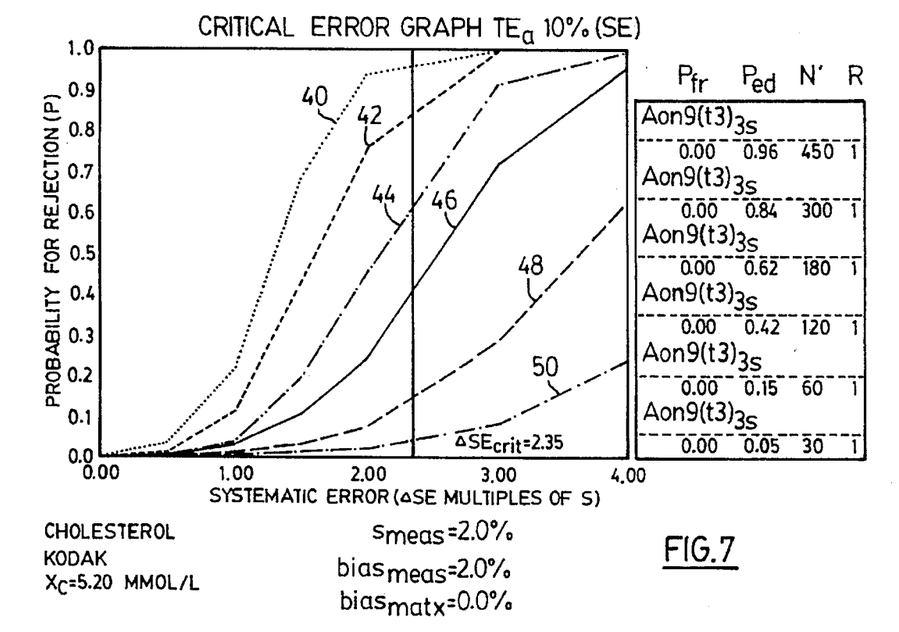
FIG. 7 is a power function graph showing the probability of error detection versus systematic error for various numbers of patient samples.

The FIG. 7 graph is for cholesterol. The target value $x_c$ is 5.2 mmol/L and the total allowable systematic error $TE_a$ is 10%. The imprecision $s_{meas}$ is 2.0% and the inaccuracy in the measure process is defined by $bias_{meas}=2.0\%$ and $bias_{matx}=0.0\%$.

In the table at the right hand side of FIG. 7, the listing "Aon9" indicates that in the average of normals method, the ratio $s_p/s_a$ for the analyte in question (cholesterol) is 9. The symbol "t3" indicates that the truncation limits are 3 standard deviations (meaning that patient results outside 3 standard deviations from the normal mean are excluded or truncated from the data, to protect the data from abnormal results). The subscript "3s" indicates that a 3s control limit has been used, resulting in a probability of false rejection $P_{fr}$ which is essentially zero.

Six curves 40 to 50 respectively are shown for N' ranging from 450 to 30 respectively. Again and as expected, a larger N' yields a higher probability of error detection. It will be seen that for a calculated $\Delta SE_{crit}$ value of 2.35, and if the desired probability of error detection is 90%, N' should be slightly higher than 300 but may be less than 450.

Figure 8A:
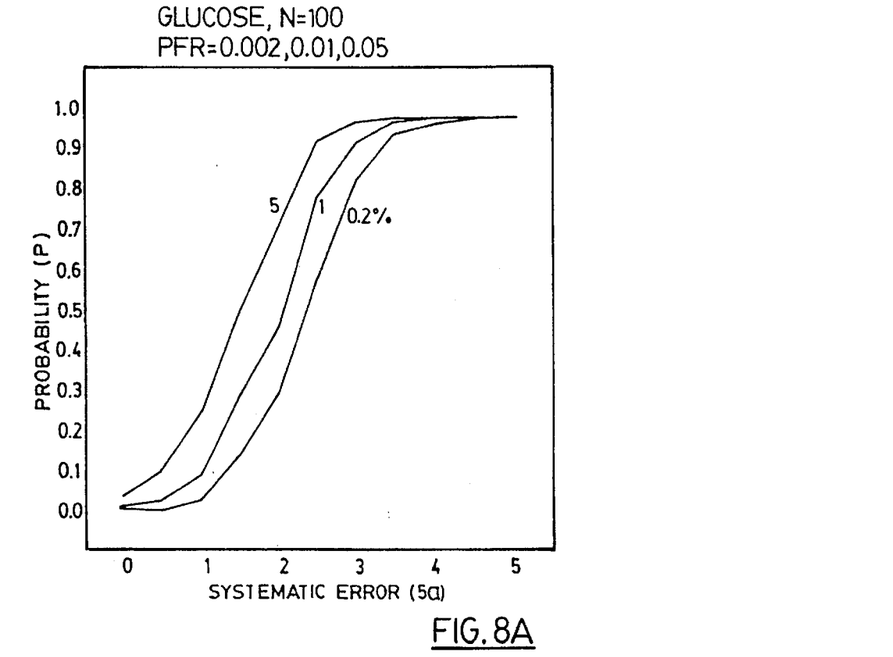
FIGS. 8A and 8B are power function graphs showing the effect of the probability of false rejection on the probability for detecting analyte errors.
Figure 8B:
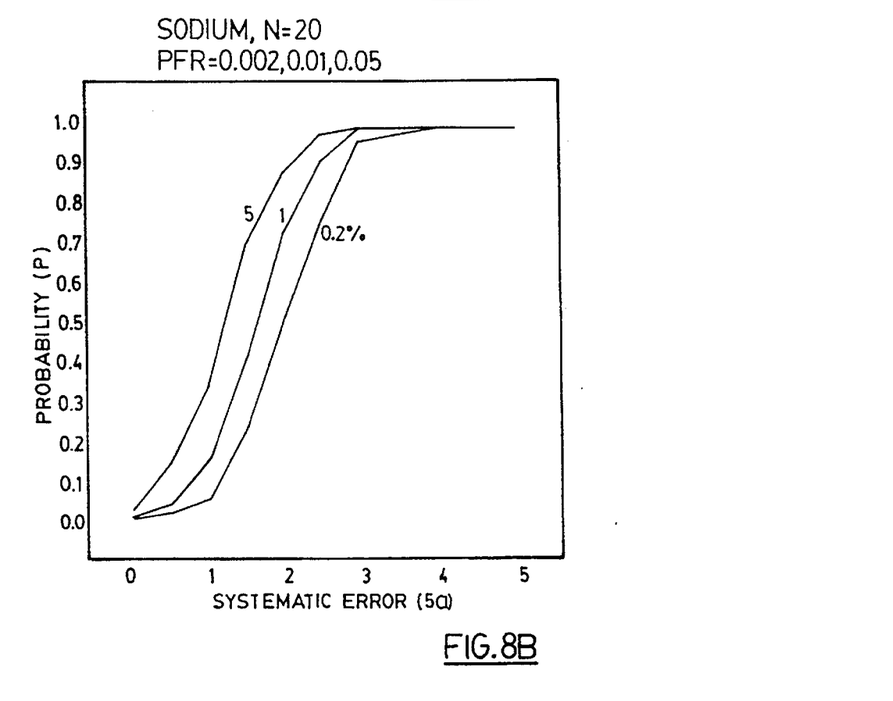

As further shown in the Cembrowski et al. paper, FIGS. 8A and 8B show the effect of varying the control limits for glucose (N'=100) and sodium (N'=20). In each case the bottom curve in each graph corresponds to control limits calculated as 2.09 times the standard error ($SE_{mean}$) of the mean, which provides a false rejection rate of 0.2% (marked on the graphs). The middle curve is for 2.58 $SE_{mean}$ control limits or 1.0% false rejections (marked on the graphs), and the upper curves are for 1.96 $SE_{mean}$ or 5.0% false rejections. With the invention, as mentioned, it is desirable to have a high probability (90% or better) of determining the critical error $\Delta SE_{crit}$ for the analyte or characteristic in question, even if this results in a relatively high "false rejection" rate, since the result of a "false rejection" is simply that an unnecessary analyses of a control material has been performed.

The mean which is determined is preferably a moving average, i.e. a selected N' is used (e.g. 100). All new test results are added in determining the mean, and all test results which occurred more than N' tests previously are removed from the calculation of the mean. While a cumulative average could be used in place of a moving average, the cumulative average is likely to become too sensitive in detecting shifts as N' increases and may therefore lead to an undesirably high false rejection rate.

Thus, in the method of the invention the desired shift in patient test results which is to be detected is determined. Usually the shift will be a medically important shift and will commonly be determined from the quality standards set by a regulatory agency, e.g. the CLIA proficiency testing standards for acceptable performance, as set forth in Table 3 above. For example, for cholesterol the analytical quality standard according to CLIA requires that a test result be correct to within 10% of the target value. However, the medically important shift which is to be detected can also be determined from a clinical quality requirement (described in the form of a medically significant change in a test result, or a decision interval) as set by a customer. (The term "decision interval" is commonly used to describe the area between an acceptable value for an analyte, and a value at which follow up testing is required to determine appropriate treatment.)

Next, the size shift $\Delta SE_{crit}$ in the mean that must be detected in order to detect the desired shift in target value, is determined. To determine this, it is necessary (as discussed above) to have information about the accuracy and precision of the analysis method. Methods such as equation 1 above, or equation 3.4 in the above identified Westgard Quality Corporation publication, are preferably used to determine $\Delta SE_{crit}$. However other methods may also be used for determining the critical systematic error $\Delta SE_{crit}$ that needs to be detected in order to detect a desired shift in the target value of the patient specimen analyte or other characteristic.

In addition, the ratio $s_p/s_a$ is determined for the test in question (as discussed in Cembrowski et al.). Since $\Delta SE_{crit}$ is known, reference is then made to power curves such as those of FIGS. 4A to 4D to determine what N' is needed to have a desired probability of detecting $\Delta SE_{crit}$. Usually as mentioned the desired probability will be 90%, even if this leads to a relatively high false rejection rate. Other suitable methods can also be used to select an appropriate N'.

Then, during an analytical testing run, if observation shows that the mean of a given patient test has shifted by more than the predetermined amount $\Delta SE_{crit}$, then the next step is to insert control materials for analysis. If the analysis of the control materials verifies that the run is out of control (e.g. the control material analysis results differ from the required mean by more than $\Delta SE_{crit}$ for the control materials, or using any desired control rules), then the analyses subsequent to the previous acceptable analysis of control materials are reassessed (and usually rejected). The analyzer is then investigated and if necessary repaired and recalibrated.

If the results of the control material analysis indicate that the process is still in control, then a new run is begun and the calculation of the patient mean is restarted (or resumed). The analysis results prior to the control material analysis are accepted and reported. However the shift in the patient mean may indicate that a pre-analytical factor has affected a group of patient samples, e.g. that the specimens have waited perhaps in too high temperatures for too long before analysis, or that the patient population used had a collective problem.

It is also noted that some commercial analyzers will conduct a variety of tests, e.g. the Kodak E750-XRC analyzer will conduct at least 22 tests. In some cases a shift in the patient mean beyond $\Delta SE_{crit}$ (or beyond the selected limit chosen) may indicate a problem with that test only, and in other cases it may indicate a problem with the analyzer as a whole. Therefore as a minimum, when the patient mean on a multi-test analyzer shifts beyond the preset limit for a given test, control materials will be inserted and analyzed for that test. Depending on the inter-dependence of the tests, several or all of the tests on the analyzer will be requalified by insertion of control materials when the patient mean shifts beyond the chosen limit.

While preferred embodiments of the invention have been described, it will be appreciated that various changes can be made within the spirit of the invention.

We claim:

1. A method of controlling analyzing patient medical specimens in an analytical run, each specimen having a selected characteristic and a number representative of said characteristic, said method comprising:

(a) analyzing, on an analyzer, a plurality of said patient medical specimens to obtain, for each specimen, the number representative of said selected characteristic of said specimen;

(b) determining a size shift to be detected in said number, said size shift being a target value shift;

(c) determining a mean from at least some of said numbers;

(d) determining a size shift to be detected in said mean in order to detect said target value shift, said size sift in said mean being a preselected amount;

(e) determining whether said mean shifts by said preselected amount;

(f) providing a control material containing said selected characteristic and being of known properties;

(g) determining expected control values for said control material when said control material is analyzed on said analyzer;

(h) ending said analytical run if said mean shifts by said preselected amount, by inserting said control material into said analyzer, and analyzing said control material therein;

(i) determining, from the analysis of said control material, whether said selected characteristic of said control material deviates from said expected control values by more than said predetermined amount; and (j) determining, when said control material is analyzed on said analyzer and when such analysis indicates that the selected characteristic of said control material deviates from said expected control values by more than a predetermined amount, that said analyzer is incapable of detecting said target value.

2. A method according to claim 1 wherein said target value shift is a medically important shift, and wherein said analyzer may be subject to an inaccuracy and an imprecision and wherein the step of determining a size shift further comprises, using as said preselected amount the size shift in said mean which it is necessary to detect when said analyzer is exhibiting said inaccuracy and said imprecision, in order to thereby reliably detect said medically important shift.

3. A method according to claim 2 wherein said selected characteristic in said patient medical specimens has a variability ($S_p$) and said selected characteristic in said patient medical specimens when analyzed by said analyzer has a variability ($s_p$), and wherein said method further includes the step of determining the ratio $s_p/s_a$, and wherein step (c) further comprises choosing the number of said medical specimens used to obtain said mean whereby when said ratio there is a desired probability of determining whether said mean has shifted by more than said preselected amount.

4. A method according to claim 3 wherein said predetermined amount is $\Delta SE_{crit}$ and is determined by the relationship $\Delta SE_{crit}=[(TE_{PT} -\text{bias})/s_{meas}]-z$, where: $TE_{PT}$ is said medically important shift, bias is a measure of said inaccuracy, $s_{meas}$ is a measure of said imprecision, and z is a value indicative of a permitted defect rate.

5. A method according to claim 3 wherein said desired probability is at least 90%.

6. A method according to claim 1 further comprising the steps of reporting, if said selected characteristic of said control material does not deviate from said expected control values by more than said predetermined amount, the analyses of patient medical specimens analyzed in said analyzer prior to the analysis of said control material and resuming analysis of patient medical specimens by said analyzer, but not reporting, if said selected characteristic of said control material deviates from said expected control values by more than said predetermined amount, at least some of the analyses of patient medical specimens performed prior to the analysis of said control material.

7. A method according to claim 6 wherein said selected characteristic is the presence of a selected substance in said specimen.

8. A method according to claim 7 wherein said number represents the concentration of said selected substance in said specimen.

9. A method according to claim 7 wherein said substance is selected from the group comprising acid phosphatase, albumin, alkaline phosphatase, ALT (alanine transaminase), amalase, AST (aspartate transaminase), bilirubin, urea, calcium, cholesterol, creatine kinase, chloride, carbon dioxide, creatinine, iron, GGT (gamma glutamyl transferase), glucose, HDL (high density lipid)—cholesterol, lithium, lipase, potassium, LD (lactate dehydrogenase), magnesium, sodium, phosphate, triglyceride, total protein, urate, digoxin, ferritin, folate, free T4 (free thyroxine), FSH (follitropin hormone), hCG (human chorionic gonadotropin), IgE (immunoglobulin E), LH (lutropin hormone), prolactin, salicylate, total T4 (total thyroxine), TSH (thyrotropin stimulating hormone), total T3 (total triiodothyroxine), vitamin B12, WBC (white blood cells), RBC (red blood cells), platelets, MCV (mean cell volume), HCT (hematocrit), Hb (hemoglobin), PT/INR (prothrombin time/INR), and APTT (activated partial thromboplastin time).

* * * * *